(12) United States Patent
Carcieri et al.

(10) Patent No.: US 10,518,093 B2
(45) Date of Patent: Dec. 31, 2019

(54) METHOD AND APPARATUS FOR PROGRAMMING NEUROMODULATION DEVICES

(71) Applicant: Boston Scientific Neuromodulation Corporation, Valencia, CA (US)

(72) Inventors: Stephen Carcieri, Los Angeles, CA (US); Michael A. Moffitt, Saugus, CA (US); Peter J. Yoo, Burbank, CA (US); Dennis Allen Vansickle, Lancaster, CA (US); Sridhar Kothandaraman, Valencia, CA (US); Michael Andrew Caruso, Los Angeles, CA (US); Dean Chen, Irvine, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 36 days.

(21) Appl. No.: 15/691,277

(22) Filed: Aug. 30, 2017

(65) Prior Publication Data

US 2017/0361104 A1 Dec. 21, 2017

Related U.S. Application Data

(63) Continuation of application No. 15/134,212, filed on Apr. 20, 2016, now Pat. No. 9,750,939.
(Continued)

(51) Int. Cl.
*A61N 1/00* (2006.01)
*A61N 1/36* (2006.01)
(Continued)

(52) U.S. Cl.
CPC ..... *A61N 1/36171* (2013.01); *A61N 1/36128* (2013.01); *A61N 1/37247* (2013.01);
(Continued)

(58) Field of Classification Search
CPC .............. A61N 1/3605; A61N 1/36062; A61N 1/36071; A61N 1/3614; A61N 1/36146; A61N 1/37247
See application file for complete search history.

(56) References Cited

U.S. PATENT DOCUMENTS

| | | |
|---|---|---|
| 6,516,227 B1 | 2/2003 | Meadows et al. |
| 6,920,359 B2 | 7/2005 | Meadows et al. |

(Continued)

FOREIGN PATENT DOCUMENTS

| | | |
|---|---|---|
| AU | 2016251663 B2 | 1/2019 |
| CN | 107864632 A | 3/2018 |

(Continued)

OTHER PUBLICATIONS

"U.S. Appl. No. 15/134,212, Non Final Office Action dated Jan. 17, 2017", 6 pgs.

(Continued)

*Primary Examiner* — Scott M. Getzow
(74) *Attorney, Agent, or Firm* — Schwegman Lundberg & Woessner, P.A.

(57) ABSTRACT

An example of a system for delivering neurostimulation pulses to a patient using a plurality of electrodes and controlling the delivery of the neurostimulation pulses by a user may include a programming control circuit and a user interface. The programming control circuit may be configured to generate a plurality of stimulation parameters controlling delivery of neurostimulation pulses according to one or more stimulation waveforms. The interface may include a display screen and an interface control circuit. The interface control circuit may be configured to define the one or more stimulation waveforms, and may include an impedance presentation module. The impedance presentation module may be configured to determine values of impedances each between two electrodes of the plurality of (Continued)

electrodes for all of combinations of two electrodes available from the plurality of electrodes and display the determined values of impedances on the display screen.

20 Claims, 9 Drawing Sheets

Related U.S. Application Data

(60) Provisional application No. 62/273,508, filed on Dec. 31, 2015, provisional application No. 62/150,935, filed on Apr. 22, 2015.

(51) Int. Cl.
*A61N 1/372* (2006.01)
*G06F 19/00* (2018.01)
*G16H 40/63* (2018.01)
*A61N 1/05* (2006.01)

(52) U.S. Cl.
CPC ......... *G06F 19/3481* (2013.01); *G16H 40/63* (2018.01); *A61N 1/0534* (2013.01); *A61N 1/0551* (2013.01); *A61N 1/36146* (2013.01)

(56) References Cited

U.S. PATENT DOCUMENTS

| | | | |
|---|---|---|---|
| 7,369,899 B2 | 5/2008 | Malinowski et al. | |
| 7,957,808 B2 | 6/2011 | Dawant et al. | |
| 9,072,897 B2 * | 7/2015 | Sachs | A61N 1/36003 |
| 9,750,939 B2 | 9/2017 | Carcieri et al. | |
| 2005/0245987 A1 | 11/2005 | Woods et al. | |
| 2007/0142872 A1 | 6/2007 | Mickle et al. | |
| 2009/0287271 A1 | 11/2009 | Blum et al. | |
| 2010/0280572 A1 | 11/2010 | Meadows et al. | |
| 2011/0264165 A1 | 10/2011 | Molnar et al. | |
| 2012/0271376 A1 | 10/2012 | Kokones et al. | |
| 2012/0302912 A1 * | 11/2012 | Moffitt | A61N 1/36185 600/554 |
| 2013/0131760 A1 | 5/2013 | Rao et al. | |
| 2013/0218237 A1 | 8/2013 | Svirsky | |
| 2014/0066999 A1 | 3/2014 | Carcieri et al. | |
| 2014/0067018 A1 | 3/2014 | Caercieri et al. | |
| 2014/0067022 A1 | 3/2014 | Carcieri et al. | |
| 2014/0249599 A1 | 9/2014 | Kaula et al. | |
| 2016/0310743 A1 | 10/2016 | Carcieri et al. | |

FOREIGN PATENT DOCUMENTS

| | | |
|---|---|---|
| EP | 2567729 A1 | 3/2013 |
| JP | 2008535620 A | 9/2008 |
| JP | 2013527784 A | 7/2013 |
| JP | 2018516633 A | 6/2018 |
| WO | WO-2013152124 A1 | 10/2013 |
| WO | WO-2016172239 A1 | 10/2016 |

OTHER PUBLICATIONS

"U.S. Appl. No. 15/134,212, Notice of Allowance dated May 2, 2017", 6 pgs.
"U.S. Appl. No. 15/134,212, Response filed Apr. 10, 2017 to Non Final Office Action dated Jan. 17, 2017", 10 pgs.
"International Application Serial No. PCT/US2016/028484, International Search Report dated Jul. 19, 2016", 5 pgs.
"International Application Serial No. PCT/US2016/028484, Written Opinion dated Jul. 19, 2016", 5 pgs.
Vansickle, Dennis Allen, "Deep Brain Stimulation Clinical Effects Map With Visual Indicators for Patient Amplitude Limits", U.S. Appl. No. 62/130,037, filed Mar. 9, 2015.
"Australian Application Serial No. 2016251663, First Examination Report dated Dec. 18, 2017", 4 pgs.
"Australian Application Serial No. 2016251663, Response filed Aug. 29, 2018 to First Examination Report dated Dec. 18, 2017", 18 pgs.
"European Application Serial No. 16721028.5, Response filed Jun. 13, 2018 to Communication Pursuant to Rules 161 and 162 EPC dated Dec. 8, 2017", 12 pgs.
"International Application Serial No. PCT/US2016/028484, International Preliminary Report on Patentability dated Nov. 2, 2017", 7 pgs.
"Japanese Application Serial No. 2017-555485, Notification of Reasons for Refusal/Rejection dated Nov. 12, 2018", W/ English Translation, 8 pgs.
"Japanese Application Serial No. 2017-555485, Response filed Feb. 5, 2019 to Notification of Reasons for Refusal/Rejection dated Nov. 12, 2018", w/ English claims, 7 pgs.
"European Application Serial No. 19175427.4, Extended European Search Report dated Sep. 12, 2019", 9 pgs.

\* cited by examiner

| | E1 | E2 | E3 | E4 | E5 | E6 | E7 | E8 |
|---|---|---|---|---|---|---|---|---|
| | | | | N-POLAR IMPEDANCE (Ω) — 856 | | | | |
| E1 | 500 | 589 | 604 | 634 | 650 | 670 | 676 | 690 |
| E2 | | 524 | 622 | 634 | 667 | 700 | 702 | 698 |
| E3 | | | 456 | 610 | 620 | 680 | 705 | 716 |
| E4 | | | | 399 | 590 | 598 | 660 | 700 |
| E5 | | | | | 467 | 590 | 580 | 690 |
| E6 | | | | | | 489 | 524 | 702 |
| E7 | | | | | | | 569 | 680 |
| E8 | | | | | | | | 665 |

1372          856
                             RATE (Hz)

1374    | 2   | 30 | 60 | 66  | 128 | 154 | 198 |
1376    | 6   | 34 | 63 | 71  | 130 | 159 | 204 |
1378    | 10  | 37 | 74 | 99  | 132 | 170 | 208 |
        | 15  | 40 | 76 | 112 | 136 | 174 | 223 |
        | 17  | 45 | 79 | 113 | 139 | 176 | 227 |
        | 20  | 50 | 85 | 104 | 143 | 179 | 231 |
        | 22  | 53 | 89 | 116 | 146 | 185 | 238 |
        | 26  | 57 | 95 | 119 | 149 | 190 | 255 |

CANCEL

*FIG. 13*

METHOD AND APPARATUS FOR PROGRAMMING NEUROMODULATION DEVICES

CLAIM OF PRIORITY

This application is a continuation of U.S. application Ser. No. 15/134,212, filed Apr. 20, 2016, which claims the benefit of priority to U.S. Provisional Patent Application Ser. No. 62/273,508, filed on Dec. 31, 2015 and U.S. Provisional Patent Application Ser. No. 62/150,935, filed Apr. 22, 2015, each of which is incorporated herein by reference in its entirety.

TECHNICAL FIELD

This document relates generally to neurostimulation and more particularly to a neurostimulation system including various features facilitating programming of stimulation devices for neuromodulation with safe and efficacious settings.

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device is used to program the implantable neurostimulator with stimulation parameters controlling the delivery of the neurostimulation energy.

In one example, the neurostimulation energy is delivered in the form of electrical neurostimulation pulses. The delivery is controlled using stimulation parameters that specify spatial (where to stimulate), temporal (when to stimulate), and informational (patterns of pulses directing the nervous system to respond as desired) aspects of a pattern of neurostimulation pulses. The human nervous systems use neural signals having sophisticated patterns to communicate various types of information, including sensations of pain, pressure, temperature, etc. It may interpret an artificial stimulation with a simple pattern of stimuli as an unnatural phenomenon, and respond with an unintended and undesirable sensation and/or movement. Also, as the condition of the patient may change while receiving a neurostimulation therapy, the pattern of neurostmulation pulses applied to the patient may need to be changed to maintain efficacy of the therapy while minimizing the unintended and undesirable sensation and/or movement. While modern electronics can accommodate the need for generating sophisticated pulse patterns that emulate natural patterns of neural signals observed in the human body, the capability of a neurostimulation system depends on its post-manufacturing programmability to a great extent. For example, a sophisticated pulse pattern may only benefit a patient when it is customized for that patient and updated timely in response to changes in the patient's conditions and needs. This makes programming of a stimulation device for a patient a challenging task.

SUMMARY

An example (e.g., "Example 1") of a system for delivering neurostimulation pulses to a patient using a plurality of electrodes and controlling the delivery of the neurostimulation pulses by a user may include a programming control circuit and a user interface. The programming control circuit may be configured to generate a plurality of stimulation parameters controlling delivery of neurostimulation pulses according to one or more stimulation waveforms. The interface may include a display screen and an interface control circuit. The interface control circuit may be configured to define the one or more stimulation waveforms, and may include an impedance presentation module. The impedance presentation module may be configured to determine values of impedances each between two electrodes of the plurality of electrodes for all of combinations of two electrodes available from the plurality of electrodes and display the determined values of impedances on the display screen.

In Example 2, the subject matter of Example 1 may optionally be configured to further include an implantable stimulator and an implantable lead. The implantable stimulator may include a stimulation output circuit configured to deliver the neurostimulation pulses and a stimulation control circuit configured to control the delivery of the neurostimulation pulses using the plurality of stimulation parameters. The implantable lead may be configured to be connected to the implantable stimulator and include a plurality of lead electrodes of the plurality of electrodes.

In Example 3, the subject matter of Example 2 may optionally be configured such that the implantable stimulator further includes a reference electrode of the plurality of electrodes, and the impedance presentation module is configured to determine and display values of monopolar impedances each between an electrode of the plurality of lead electrodes and the reference electrode and values of bipolar impedances each between two electrodes of the plurality of lead electrodes.

In Example 4, the subject matter of Example 3 may optionally be configured such that the impedance presentation module is configured display the determined values of impedances on the display screen in a matrix showing all the monopolar impedances and bipolar impedances with the monopolar impedances shown along the diagonal of the matrix.

In Example 5, the subject matter of any one or any combination of Examples 2-4 may optionally be configured such that the stimulation output circuit includes a plurality of timing channels each configured to deliver pulses of the neurostimulation pulses when being programmed to be active and not to deliver pulses of the neurostimulation pulses when being programmed to be inactive, and the interface control circuit includes a channel timing module configured to identify one or more transition points in the one or more stimulation waveforms at which a timing channel of the plurality of timing channels becomes active or becomes inactive and apply a turn-off period during which none of the neurostimulation pulse is delivered from any active channel of the plurality of timing channels to each point of the identified one or more transition points, so that relative timing between the pulses delivered from channels that remain active before and after a point of the identified one or more transition points remain unchanged.

In Example 6, the subject matter of any one or any combination of Examples 2-4 may optionally be configured to further include an external programming device configured to be communicatively coupled to the implantable stimulator via telemetry. The external programming device includes the programming control circuit and the user interface.

In Example 7, the subject matter of Example 6 may optionally be configured such that the external programming device is configured to be communicatively coupled to the implantable stimulator via a wireless communication link using far-field radio frequency telemetry.

In Example 8, the subject matter of any one or any combination of Examples 6 and 7 may optionally be configured such that the external programming device is configured to transmit patient information to the implantable stimulator via the wireless communication link, and the implantable stimulator further includes an implant storage device configured to store the received patient information, the patient information including portions of the patient's electronic medical records.

In Example 9, the subject matter of Example 8 may optionally be configured such that the implantable stimulator is configured to produce data to add to the patient information stored in the implant storage device.

In Example 10, the subject matter of Example 8 may optionally be configured such that the interface control circuit includes a patient data module configured to allow the user to retrieve the patient information from the implantable stimulator using the user interface. The patient data module may be configured to allow the user to select portions of the patient information for presentation using the display screen.

In Example 11, the subject matter of any one or any combination of Examples 1-10 may optionally be configured such that the interface control circuit includes an amplitude assignment module configured to assign pulse amplitudes each to an electrode of a set of electrodes selected from the plurality of electrodes for delivering a pulse of the neurostimulation pulses in terms of absolute values.

In Example 12, the subject matter of any one or any combination of Examples 1-11 may optionally be configured such that the interface control circuit includes a clinical effects map configuration module configured to configure a clinic effects map indicative of therapeutic effects and side effects estimated for the one or more stimulation waveforms.

In Example 13, the subject matter of Example 12 may optionally be configured such that the clinical effects map configuration module is configured to receive a selection of an indication for neurostimulation and automatically update the therapeutic effects based on the selected indication.

In Example 14, the subject matter of Example 12 may optionally be configured such that the clinical effects map configuration module is configured to receive a selection of a target for neurostimulation or a selection of an indication for the neurostimulation and automatically update the side effects based on the selected target or the selected indication.

In Example 15, the subject matter of any one or any combination of Examples 1-10 may optionally be configured such that the interface control circuit includes an amplitude tracking module configured to allow the user to set minimum and maximum pulse amplitudes for the neurostimulation pulses using the user interface.

An example (e.g., "Example 16") for programming an implantable stimulator to deliver neurostimulation pulses to a patient using a plurality of electrodes is also provided. The method includes programming an implantable stimulator for delivering electrical pulses through a plurality of electrodes using an external programming device, and presenting information for the programming using the user interface of the external programming device. The presentation of the information includes displaying values of impedances each between two electrodes of the plurality of electrodes for all of combinations of two electrodes available from the plurality of electrodes and displaying the determined values of impedances on the display screen.

In Example 17, the subject matter of Example 16 may optionally include delivering the electrical pulses using a plurality of timing channels of the implantable stimulator, the plurality of timing channels each configured to deliver one or more of the electrical pulses when being programmed to be active and none of the electrical pulses when being programmed to be inactive, identifying one or more transition points in the one or more stimulation waveforms at which a timing channel of the plurality of timing channels becomes active or becomes inactive, and applying a turn-off period during which none of the electrical pulse is delivered from any active channel of the plurality of timing channels to each point of the identified one or more transition points, so that relative timing between the pulses delivered from channels that remain active before and after a point of the identified one or more transition points remain unchanged.

In Example 18, the subject matter of any one or any combination of Examples 16 and 17 may optionally include providing for wireless communication between the implantable stimulation and the external programming device using far-field radio frequency telemetry.

In Example 19, the subject matter of any one or any combination of Examples 16-18 may optionally include transmitting patient information to the implantable stimulator via the wireless communication link and storing the received patient information in a storage device in the implantable stimulator. The patient information includes portions of the patient's electronic medical records including information specific to indications for neurostimulation.

In Example 19, the subject matter of any one or any combination of Examples 16-19 may optionally include assigning pulse amplitudes each to an electrode of a set of electrodes selected from the plurality of electrodes for delivering a pulse of the electrical pulses in terms of absolute values.

In Example 20, the subject matter of any one or any combination of Examples 16-19 may optionally include automatically configuring a clinic effects map indicative of therapeutic effects and side effects estimated for the one or more stimulation waveforms based on a selection of a target for neurostimulation or a selection of an indication for the neurostimulation.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

FIG. 13 illustrates an embodiment of portions of a screen displaying a stimulation rate table.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses, among other things, a neurostimulation system with programming rules, user interface, and other features that facilitate programming of stimulation devices for delivering neuromodulation to each patient with safe and efficacious settings. In various embodiments, the neurostimulation system can include an implantable device configured to deliver neurostimulation (also referred to as neuromodulation) therapies (such as deep brain stimulation (DBS), spinal cord stimulation (SCS), peripheral nerve stimulation (PNS), and vagus nerve stimulation (VNS)) and one or more external devices configured to program the implantable device for its operations and monitor the performance of the implantable device. While DBS is discussed as a specific example, the present subject matter can also be applied to facilitate programming of stimulation devices for delivering various types of neurostimulation therapies. In general, various aspects of the present subject matter as discussed in this document may be applied to any medical system that delivers electrical stimulation to a patient in various embodiments. It is also to be understood that various features of the neurostimulation are discussed in this documents as examples of techniques developed to simplify and/or improve selected aspects of programming of the stimulation devices, rather than all the features needed for the programming.

Figure 1:
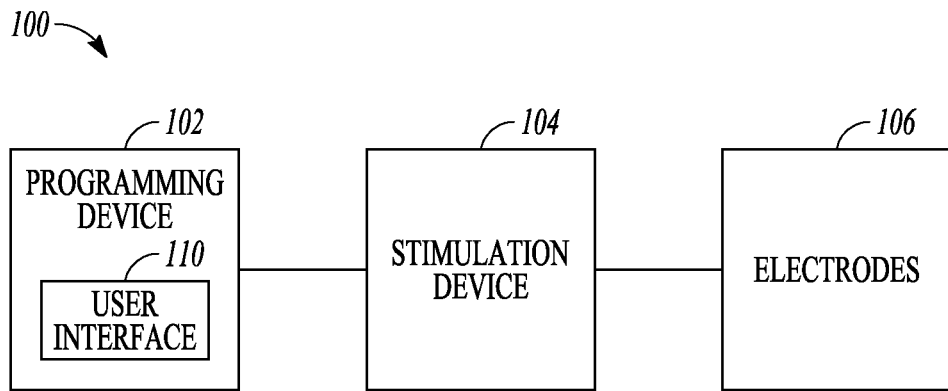
FIG. 1 illustrates an embodiment of a neurostimulation system.

FIG. 1 illustrates an embodiment of a neurostimulation system 100. System 100 includes electrodes 106, a stimulation device 104, and a programming device 102. Electrodes 106 are configured to be placed on or near one or more neural targets in a patient. Stimulation device 104 is configured to be electrically connected to electrodes 106 and deliver neurostimulation energy, such as in the form of electrical pulses, to the one or more neural targets though electrodes 106. The delivery of the neurostimulation is controlled by using a plurality of stimulation parameters, such as stimulation parameters specifying a pattern of the electrical pulses and a selection of electrodes through which each of the electrical pulses is delivered. In various embodiments, at least some parameters of the plurality of stimulation parameters are programmable by a user, such as a physician or other caregiver who treats the patient using system 100. Programming device 102 provides the user with accessibility to the user-programmable parameters. In various embodiments, programming device 102 is configured to be communicatively coupled to stimulation device via a wired or wireless link.

In this document, a "user" includes a physician or other clinician or caregiver who treats the patient using system 100; a "patient" includes a person who receives or is intended to receive neurostimulation delivered using system 100. In various embodiments, the patient is allowed to adjust his or her treatment using system 100 to certain extent, such as by adjusting certain therapy parameters and entering feedback and clinical effects information.

In various embodiments, programming device 102 includes a user interface 110 that allows the user to control the operation of system 100 and monitor the performance of system 100 as well as conditions of the patient including responses to the delivery of the neurostimulation. The user can control the operation of system 100 by setting and/or adjusting values of the user-programmable parameters.

In various embodiments, user interface 110 includes a graphical user interface (GUI) that allows the user to set and/or adjust the values of the user-programmable parameters by creating and/or editing graphical representations of various waveforms. Such waveforms may include, for example, a waveform representing a pattern of neurostimulation pulses to be delivered to the patient as well as individual waveforms that are used as building blocks of the pattern of neurostimulation pulses, such as the waveform of each pulse in the pattern of neurostimulation pulses. The GUI may also allow the user to set and/or adjust stimulation fields each defined by a set of electrodes through which one or more neurostimulation pulses represented by a waveform are delivered to the patient. The stimulation fields may each be further defined by the distribution of the current of each neurostimulation pulse in the waveform. In various embodiments, neurostimulation pulses for a stimulation period (such as the duration of a therapy session) may be delivered to multiple stimulation fields.

In various embodiments, system 100 can be configured for neurostimulation applications. User interface 110 can be configured to allow the user to control the operation of system 100 for neurostimulation. For example, system 100 as well as user interface 100 can be configured for DBS applications. Such DBS configuration includes various features that may simplify the task of the user in programming stimulation device 104 for delivering DBS to the patient, such as the features discussed in this document.

Figure 2:
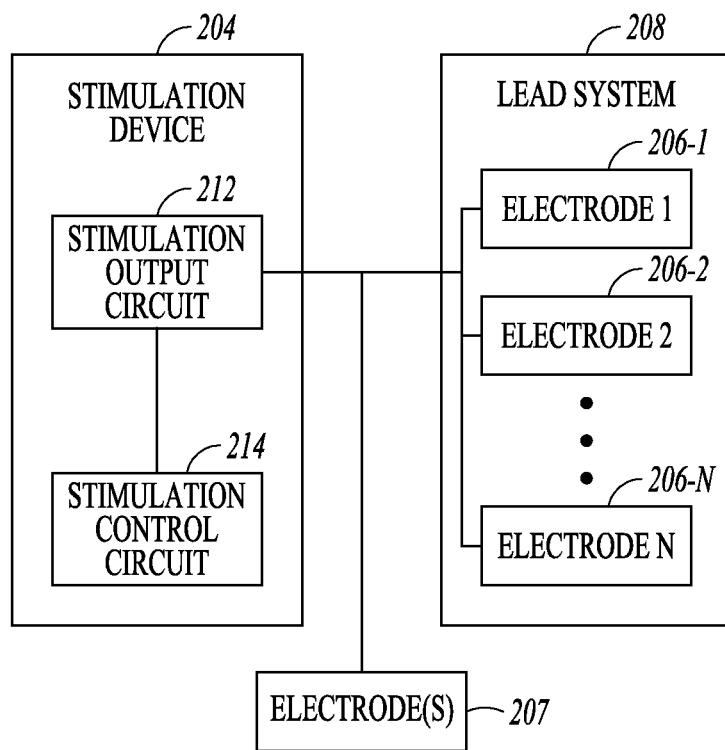
FIG. 2 illustrates an embodiment of a stimulation device and a lead system, such as may be implemented in the neurostimulation system of FIG. 1.

FIG. 2 illustrates an embodiment of a stimulation device 204 and a lead system 208, such as may be implemented in neurostimulation system 100. Stimulation device 204 represents an embodiment of stimulation device 104 and includes a stimulation output circuit 212 and a stimulation control circuit 214. Stimulation output circuit 212 produces and delivers neurostimulation pulses. Stimulation control circuit 214 controls the delivery of the neurostimulation pulses from stimulation output circuit 212 using the plurality of stimulation parameters, which specifies a pattern of the neurostimulation pulses. Lead system 208 includes one or more leads each configured to be electrically connected to stimulation device 204 and a plurality of electrodes 206 distributed in the one or more leads. The plurality of electrodes 206 includes electrode 206-1, electrode 206-2, . . . electrode 206-N, each a single electrically conductive contact providing for an electrical interface between stimulation output circuit 212 and tissue of the patient, where N≥2. The neurostimulation pulses are each delivered from stimulation output circuit 212 through a set of electrodes selected from electrodes 206. In various embodiments, the neurostimulation pulses may include one or more individually defined pulses, and the set of electrodes may be individually definable by the user for each of the individually defined pulses or each of collections of pulse intended to be delivered using the same combination of electrodes. In various embodiments, one or more additional electrodes 207 (each of which may be referred to as a reference electrode) can be electrically connected to stimulation device 204, such as one or more electrodes each being a portion of or otherwise incorporated onto a housing of stimulation device 204. Monopolar stimulation uses a monopolar electrode configuration with one or more electrodes selected from electrodes 206 and at least one electrode from electrode(s) 207. Bipolar stimulation uses a bipolar electrode configuration with two electrodes selected from electrodes 206 and none electrode(s) 207. Multipolar stimulation uses a multipolar electrode configuration with multiple (two or more) electrodes selected from electrodes 206 and none of electrode(s) 207.

In various embodiments, the number of leads and the number of electrodes on each lead depend on, for example, the distribution of target(s) of the neurostimulation and the need for controlling the distribution of electric field at each target. In one embodiment, lead system 208 includes 2 leads each having 8 electrodes.

Figure 3:
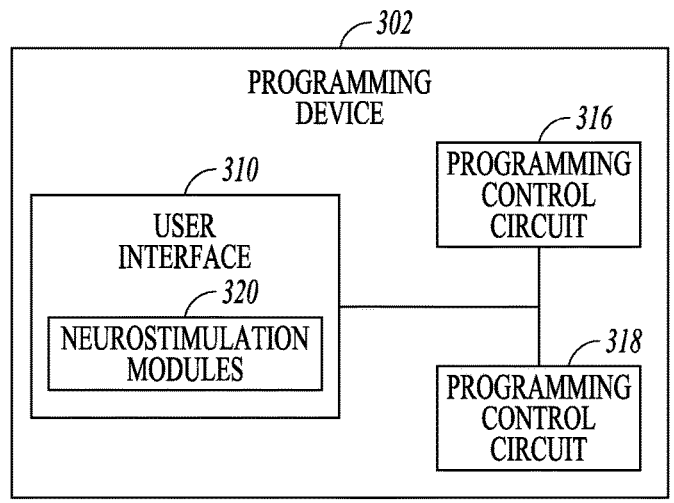
FIG. 3 illustrates an embodiment of a programming device, such as may be implemented in the neurostimulation system of FIG. 1.

FIG. 3 illustrates an embodiment of a programming device 302, such as may be implemented in neurostimulation system 100. Programming device 302 represents an embodiment of programming device 102 and includes a storage device 318, a programming control circuit 316, and a user interface 310. Storage device 318 stores one or more stimulation waveforms each represent a pattern of neurostimulation pulses to be delivered during a stimulation period. Programming control circuit 316 generates the plurality of stimulation parameters that controls the delivery of the neurostimulation pulses according to at least one of the stored one or more stimulation waveforms. User interface 310 represents an embodiment of user interface 110 and includes neurostimulation modules 320. In various embodiments, neurostimulation modules 320 are each configured to support one or more functions that facilitate programming of stimulation devices, such as stimulation device 104 including its various embodiments as discussed in this document, for delivering neurostimulation to each patient with safe and efficacious settings. Examples of such one or more functions are discussed below with references to FIG. 9.

In various embodiments, user interface 310 allows for definition of a pattern of neurostimulation pulses for delivery during a neurostimulation therapy session by creating and/or adjusting one or more stimulation waveforms using a graphical method. The definition can also include definition of one or more stimulation fields each associated with one or more pulses in the pattern of neurostimulation pulses. In various embodiments, user interface 310 includes a GUI that allows the user to define the pattern of neurostimulation pulses and perform other functions using graphical methods. In this document, "neurostimulation programming" can include the definition of the one or more stimulation waveforms, including the definition of one or more stimulation fields.

In various embodiments, circuits of neurostimulation 100, including its various embodiments discussed in this document, may be implemented using a combination of hardware and software. For example, the circuit of user interface 110, stimulation control circuit 214, programming control circuit 316, and neurostimulation modules 320, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 4:
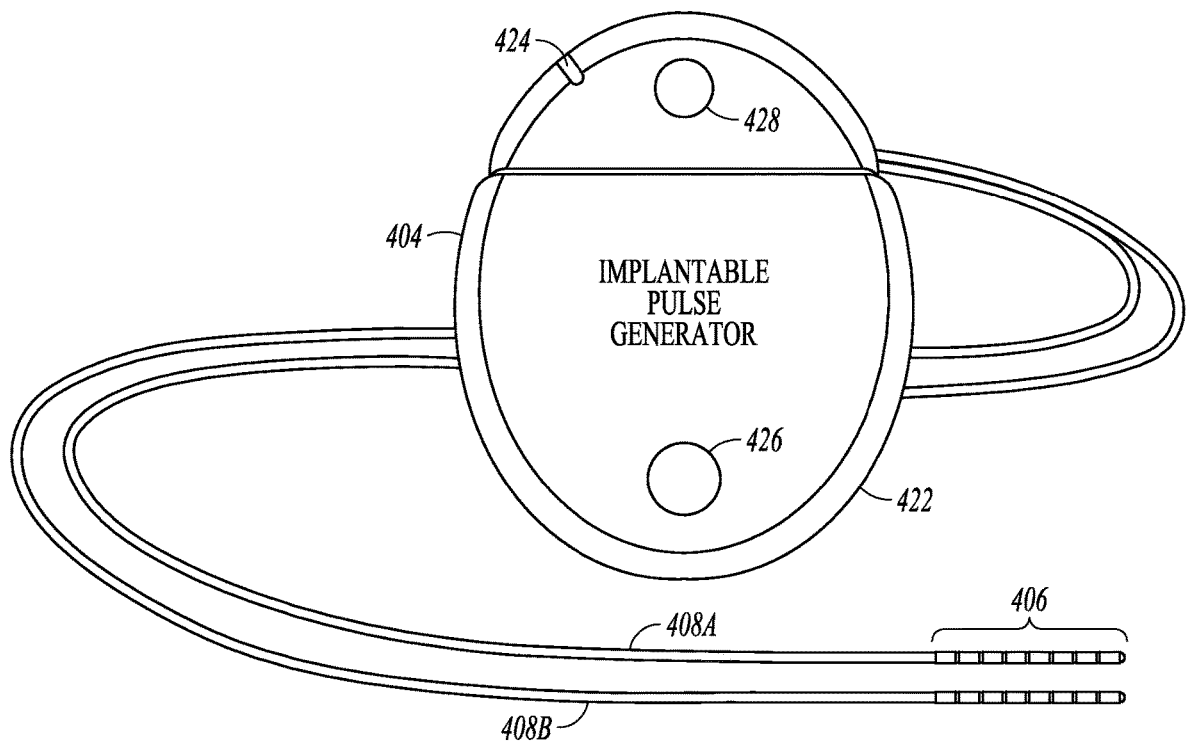
FIG. 4 illustrates an embodiment of an implantable pulse generator (IPG) and an implantable lead system, such as an example implementation of the stimulation device and lead system of FIG. 2.

FIG. 4 illustrates an embodiment of an implantable pulse generator (IPG) 404 and an implantable lead system 408. IPG 404 represents an example implementation of stimulation device 204. Lead system 408 represents an example implementation of lead system 208. As illustrated in FIG. 4, IPG 404 that can be coupled to implantable leads 408A and 408B at a proximal end of each lead. The distal end of each lead includes electrical contacts or electrodes 406 for contacting a tissue site targeted for electrical neurostimulation. As illustrated in FIG. 1, leads 408A and 408B each include 8 electrodes 406 at the distal end. The number and arrangement of leads 408A and 408B and electrodes 406 as shown in FIG. 1 are only an example, and other numbers and arrangements are possible. In various embodiments, the electrodes are ring electrodes. The implantable leads and electrodes may be configured by shape and size to provide electrical neurostimulation energy to a neuronal target included in the subject's brain, or configured to provide electrical neurostimulation energy to a nerve cell target included in the subject's spinal cord.

Figure 5:
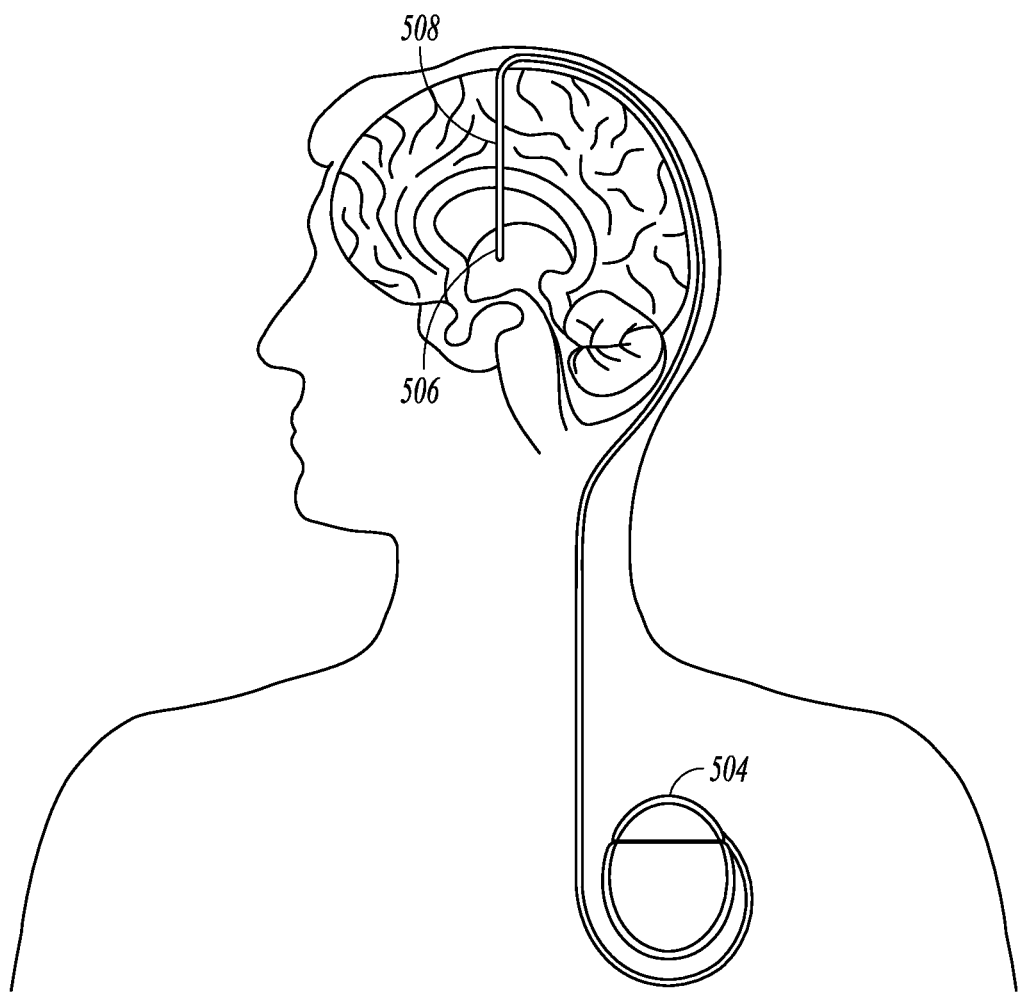
FIG. 5 illustrates an embodiment of an IPG and an implantable lead system, such as the IPG and lead system of FIG. 4, arranged to provide neurostimulation to a patient.

FIG. 5 illustrates an embodiment of an IPG 504 and an implantable lead system 508 arranged to provide neurostimulation to a patient. An example of IPG 504 includes IPG 404. An example of lead system 508 includes one or more of leads 408A and 408B. In the illustrated embodiment, implantable lead system 508 is arranged to provide Deep Brain Stimulation (DBS) to a patient, with the stimulation target being neuronal tissue in a subdivision of the thalamus of the patient's brain. Other examples of DBS targets include neuronal tissue of the globus pallidus (GPi), the subthalamic nucleus (STN), the pedunculopontine nucleus (PPN), substantia nigra pars reticulate (SNr), cortex, globus pallidus externus (GPe), medial forebrain bundle (MFB), periaquaductal gray (PAG), periventricular gray (PVG), habenula, subgenual cingulate, ventral intermediate nucleus (VIM), anterior nucleus (AN), other nuclei of the thalamus, zona incerta, ventral capsule, ventral striatum, nucleus accumbens, and any white matter tracts connecting these and other structures.

Returning to FIG. 4, the IPG 404 can include a hermetically-sealed IPG case 422 to house the electronic circuitry of IPG 404. IPG 404 can include an electrode 426 formed on IPG case 422. IPG 404 can include an IPG header 424 for coupling the proximal ends of leads 408A and 408B. IPG header 424 may optionally also include an electrode 428. Electrodes 426 and/or 428 represent embodiments of electrode(s) 207 and may each be referred to as a reference electrode. Neurostimulation energy can be delivered in a monopolar (also referred to as unipolar) mode using electrode 426 or electrode 428 and one or more electrodes selected from electrodes 406. Neurostimulation energy can be delivered in a bipolar mode using a pair of electrodes of the same lead (lead 408A or lead 408B). Neurostimulation energy can be delivered in an extended bipolar mode using one or more electrodes of a lead (e.g., one or more electrodes of lead 408A) and one or more electrodes of a different lead (e.g., one or more electrodes of lead 408B).

The electronic circuitry of IPG 404 can include a control circuit that controls delivery of the neurostimulation energy. The control circuit can include a microprocessor, a digital signal processor, application specific integrated circuit (ASIC), or other type of processor, interpreting or executing instructions included in software or firmware. The neurostimulation energy can be delivered according to specified (e.g., programmed) modulation parameters. Examples of setting modulation parameters can include, among other things, selecting the electrodes or electrode combinations used in the stimulation, configuring an electrode or electrodes as the anode or the cathode for the stimulation, specifying the percentage of the neurostimulation provided by an electrode or electrode combination, and specifying stimulation pulse parameters. Examples of pulse parameters include, among other things, the amplitude of a pulse (specified in current or voltage), pulse duration (e.g., in microseconds), pulse rate (e.g., in pulses per second), and parameters associated with a pulse train or pattern such as burst rate (e.g., an "on" modulation time followed by an "off" modulation time), amplitudes of pulses in the pulse train, polarity of the pulses, etc.

Figure 6:
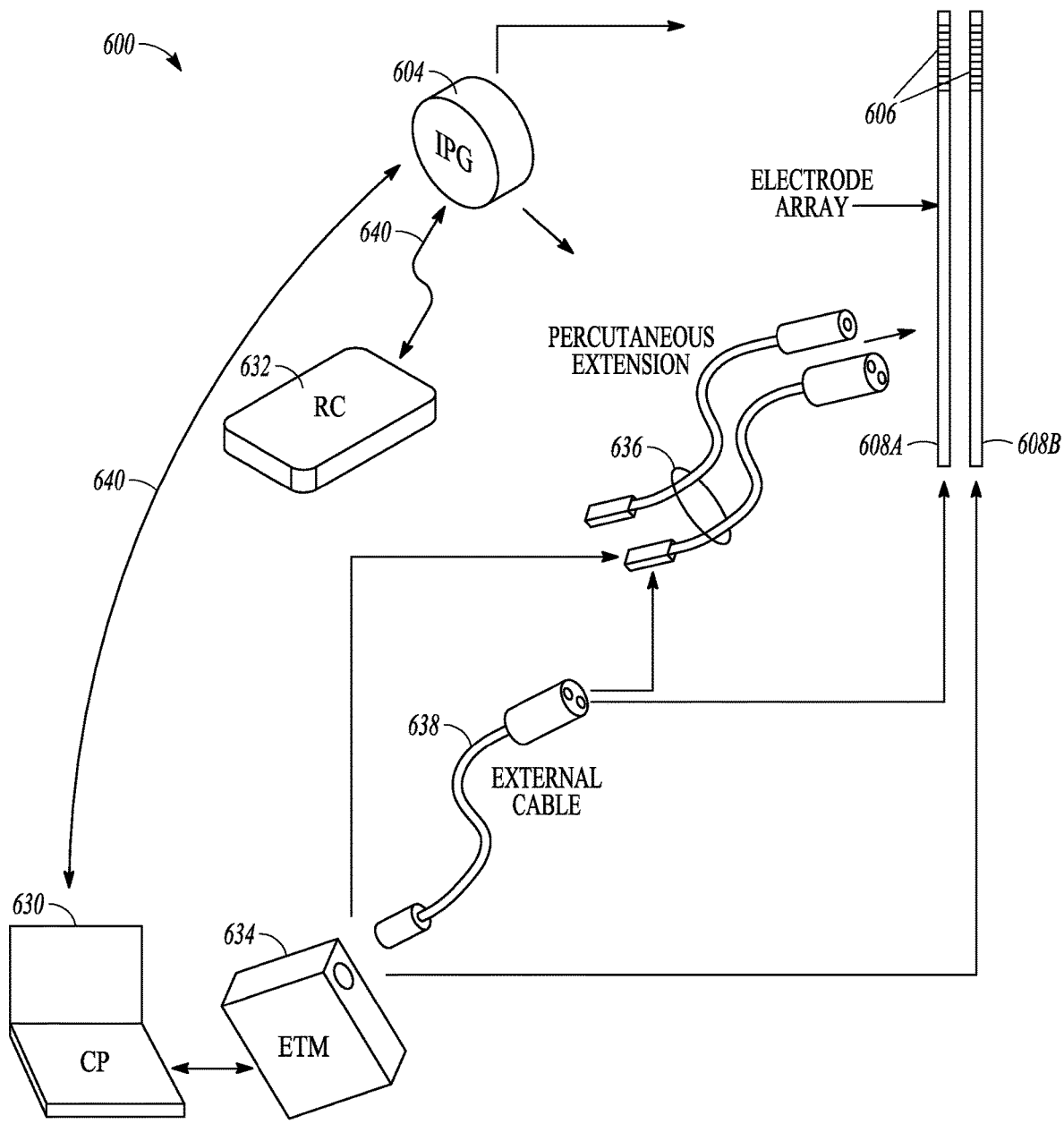
FIG. 6 illustrates an embodiment of portions of a neurostimulation system.

FIG. 6 illustrates an embodiment of portions of a neurostimulation system 600. System 600 includes an IPG 604, implantable neurostimulation leads 608A and 608B, an external remote controller (RC) 632, a clinician's programmer (CP) 630, and an external trial modulator (ETM) 634. IPG 404 may be electrically coupled to leads 608A and 608B directly or through percutaneous extension leads 636. ETM 634 may be electrically connectable to leads 608A and 608B via one or both of percutaneous extension leads 636 and/or external cable 638. System 600 represents an embodiment of system 100, with IPG 604 representing an embodiment of stimulation device 104, electrodes 606 of leads 608A and 608B representing electrodes 106, and CP 630, RC 632, and ETM 634 collectively representing programming device 102.

ETM 634 may be standalone or incorporated into CP 630. ETM 634 may have similar pulse generation circuitry as LPG 604 to deliver neurostimulation energy according to specified modulation parameters as discussed above. ETM 634 is an external device that is typically used as a preliminary stimulator after leads 408A and 408B have been implanted and used prior to stimulation with IPG 604 to test the patient's responsiveness to the stimulation that is to be provided by IPG 604. Because ETM 634 is external it may be more easily configurable than IPG 604.

CP 630 can configure the neurostimulation provided by ETM 634. If ETM 634 is not integrated into CP 630, CP 630 may communicate with ETM 634 using a wired connection (e.g., over a USB link) or by wireless telemetry using a wireless communications link 640. CP 630 also communicates with IPG 604 using a wireless communications link 640.

An example of wireless telemetry is based on inductive coupling between two closely-placed coils using the mutual inductance between these coils. This type of telemetry is referred to as inductive telemetry or near-field telemetry because the coils must typically be closely situated for obtaining inductively coupled communication. IPG 604 can include the first coil and a communication circuit. CP 630 can include or otherwise electrically connected to the second coil such as in the form of a wand that can be place near IPG 604. Another example of wireless telemetry includes a far-field telemetry link, also referred to as a radio frequency (RF) telemetry link. A far-field, also referred to as the Fraunhofer zone, refers to the zone in which a component of an electromagnetic field produced by the transmitting electromagnetic radiation source decays substantially proportionally to 1/r, where r is the distance between an observation point and the radiation source. Accordingly, far-field refers to the zone outside the boundary of r=λ/2π, where λ is the wavelength of the transmitted electromagnetic energy. In one example, a communication range of an RF telemetry link is at least six feet but can be as long as allowed by the particular communication technology. RF antennas can be included, for example, in the header of IPG 604 and in the housing of CP 630, eliminating the need for a wand or other means of inductive coupling. An example is such an RF telemetry link is a Bluetooth® wireless link.

CP 630 can be used to set modulation parameters for the neurostimulation after IPG 604 has been implanted. This allows the neurostimulation to be tuned if the requirements for the neurostimulation change after implantation. CP 630 can also upload information from IPG 604.

RC 632 also communicates with IPG 604 using a wireless link 340. RC 632 may be a communication device used by the user or given to the patient. RC 632 may have reduced programming capability compared to CP 630. This allows the user or patient to alter the neurostimulation therapy but does not allow the patient full control over the therapy. For example, the patient may be able to increase the amplitude of neurostimulation pulses or change the time that a pre-programmed stimulation pulse train is applied. RC 632 may be programmed by CP 630. CP 630 may communicate with the RC 632 using a wired or wireless communications link. In some embodiments, CP 630 is able to program RC 632 when remotely located from RC 632.

Figure 7:
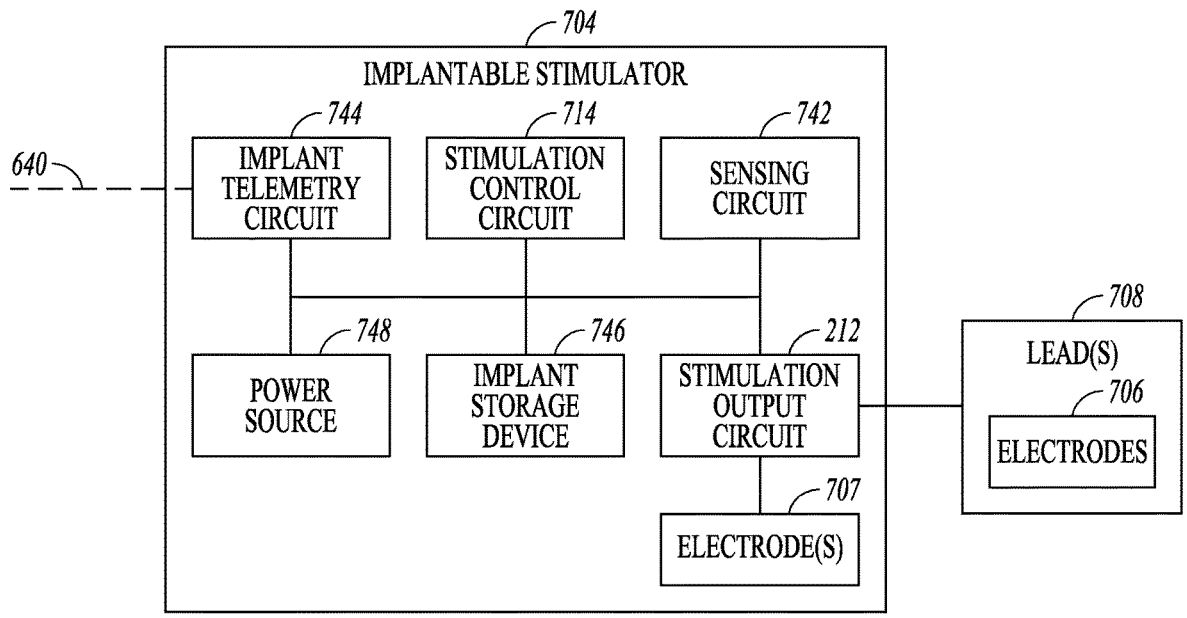
FIG. 7 illustrates an embodiment of an implantable stimulator and one or more leads of an implantable neurostimulation system, such as the implantable neurostimulation system of FIG. 6.

FIG. 7 illustrates an embodiment of implantable stimulator 704 and one or more leads 708 of an implantable neurostimulation system, such as implantable system 600. Implantable stimulator 704 represents an embodiment of stimulation device 104 or 204 and may be implemented, for example, as IPG 604. Lead(s) 708 represents an embodiment of lead system 208 and may be implemented, for example, as implantable leads 608A and 608B. Lead(s) 708 includes electrodes 706, which represents an embodiment of electrodes 106 or 206 and may be implemented as electrodes 606.

Implantable stimulator 704 may include a sensing circuit 742 that is optional and required only when the stimulator needs a sensing capability, stimulation output circuit 212, a stimulation control circuit 714, an implant storage device 746, an implant telemetry circuit 744, a power source 748, and one or more electrodes 707. Sensing circuit 742, when included and needed, senses one or more physiological signals for purposes of patient monitoring and/or feedback control of the neurostimulation. Examples of the one or more physiological signals include neural and other signals each indicative of a condition of the patient that is treated by the neurostimulation and/or a response of the patient to the delivery of the neurostimulation. Stimulation output circuit 212 is electrically connected to electrodes 706 through one or more leads 708 as well as electrodes 707, and delivers each of the neurostimulation pulses through a set of electrodes selected from electrodes 706 and electrode(s) 707. Stimulation control circuit 714 represents an embodiment of stimulation control circuit 214 and controls the delivery of the neurostimulation pulses using the plurality of stimulation parameters specifying the pattern of neurostimulation pulses. In one embodiment, stimulation control circuit 714 controls the delivery of the neurostimulation pulses using the one or more sensed physiological signals. Implant telemetry circuit 744 provides implantable stimulator 704 with wireless communication with another device such as CP 630 and RC 632, including receiving values of the plurality of stimulation parameters from the other device. Implant storage device 746 stores values of the plurality of stimulation parameters. Power source 748 provides implantable stimulator 704 with energy for its operation. In one embodiment, power source 748 includes a battery. In one embodiment, power source 748 includes a rechargeable battery and a battery charging circuit for charging the rechargeable battery. Implant telemetry circuit 744 may also function as a power receiver that receives power transmitted from an external device through an inductive couple. Electrode(s) 707 allow for delivery of the neurostimulation pulses in the monopolar mode. Examples of electrode(s) 707 include electrode 426 and electrode 418 in IPG 404 as illustrated in FIG. 4.

In one embodiment, implantable stimulator 704 is used as a master database. A patient implanted with implantable stimulator 704 (such as may be implemented as IPG 604) may therefore carry patient information needed for his or her medical care when such information is otherwise unavailable. Implant storage device 746 is configured to store such patient information. For example, the patient may be given a new RC 632 and/or travel to a new clinic where a new CP 630 is used to communicate with the device implanted in him or her. The new RC 632 and/or CP 630 can communicate with implantable stimulator 704 to retrieve the patient information stored in implant storage device 746 through implant telemetry circuit 744 and wireless communication link 640, and allow for any necessary adjustment of the operation of implantable stimulator 704 based on the retrieved patient information. In various embodiments, the patient information to be stored in implant storage device 746 may include, for example, positions of lead(s) 708 and electrodes 706 relative to the patient's anatomy (transformation for fusing computerized tomogram (CT) of postoperative lead placement to magnetic resonance imaging (MRI) of the brain), clinical effects map data, objective measurements using quantitative assessments of symptoms (for example using micro-electrode recording, accelerometers, and/or other sensors), and/or any other information considered important or useful for providing adequate care for the patient. In various embodiments, the patient information to be stored in implant storage device 746 may include data transmitted to implantable stimulator 704 for storage as part of the patient information and data acquired by implantable stimulator 704, such as by using sensing circuit 742.

In various embodiments, sensing circuit 742 (if included), stimulation output circuit 212, stimulation control circuit 714, implant telemetry circuit 744, implant storage device 746, and power source 748 are encapsulated in a hermetically sealed implantable housing or case, and electrode(s) 707 are formed or otherwise incorporated onto the case. In various embodiments, lead(s) 708 are implanted such that electrodes 706 are placed on and/or around one or more targets to which the neurostimulation pulses are to be delivered, while implantable stimulator 704 is subcutaneously implanted and connected to lead(s) 708 at the time of implantation.

Figure 8:
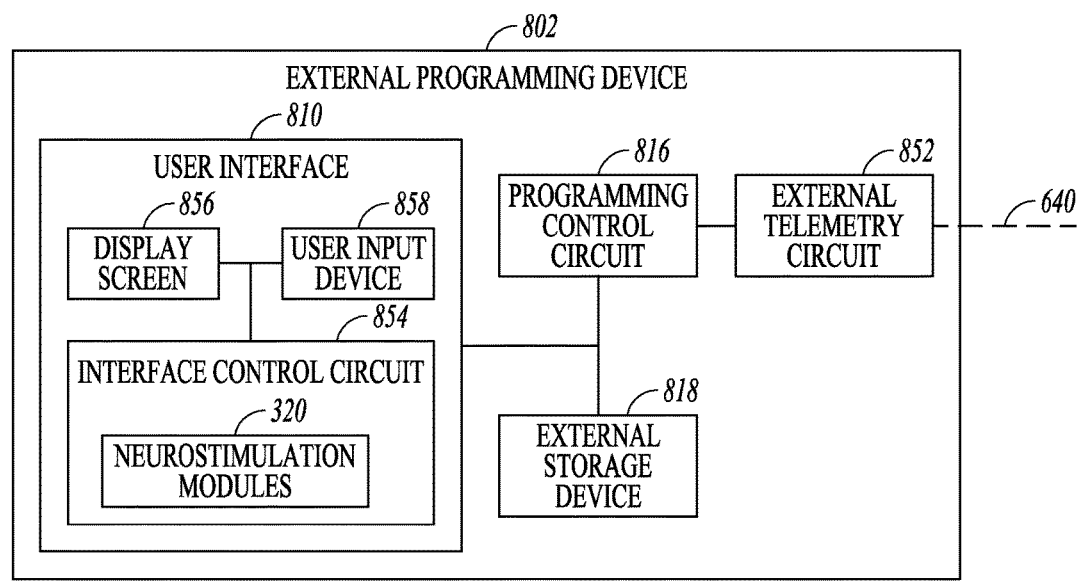
FIG. 8 illustrates an embodiment of an external programming device of an implantable neurostimulation system, such as the implantable neurostimulation system of FIG. 6.

FIG. 8 illustrates an embodiment of an external programming device 802 of an implantable neurostimulation system, such as system 600. External programming device 802 represents an embodiment of programming device 102 or 302, and may be implemented, for example, as CP 630 and/or RC 632. External programming device 802 includes an external telemetry circuit 852, an external storage device 818, a programming control circuit 816, and a user interface 810.

External telemetry circuit 852 provides external programming device 802 with wireless communication with another device such as implantable stimulator 704 via wireless communication link 640, including transmitting the plurality of stimulation parameters to implantable stimulator 704 and receiving information including the patient data from implantable stimulator 704. In one embodiment, external telemetry circuit 852 also transmits power to implantable stimulator 704 through an inductive couple.

In various embodiments, wireless communication link 640 can include an inductive telemetry link (near-field telemetry link) and/or a far-field telemetry link (RF telemetry link). For example, because DBS is often indicated for movement disorders which are assessed through patient activities, gait, balance, etc., allowing patient mobility during programming and assessment is useful. Therefore, when system 600 is intended for applications including DBS, wireless communication link 640 includes at least a far-field telemetry link that allows for communications between external programming device 802 and implantable stimulator 704 over a relative long distance, such as up to about 20 meters. External telemetry circuit 852 and implant telemetry circuit 744 each include an antenna and RF circuitry configured to support such wireless telemetry.

External storage device 818 stores one or more stimulation waveforms for delivery during a neurostimulation therapy session, such as a DBS therapy session, as well as various parameters and building blocks for defining one or more waveforms. The one or more stimulation waveforms may each be associated with one or more stimulation fields and represent a pattern of neurostimulation pulses to be delivered to the one or more stimulation field during the neurostimulation therapy session. In various embodiments, each of the one or more stimulation waveforms can be selected for modification by the user and/or for use in programming a stimulation device such as implantable stimulator 704 to deliver a therapy. In various embodiments, each waveform in the one or more stimulation waveforms is definable on a pulse-by-pulse basis, and external storage device 818 may include a pulse library that stores one or more individually definable pulse waveforms each defining a pulse type of one or more pulse types. External storage device 818 also stores one or more individually definable stimulation fields. Each waveform in the one or more stimulation waveforms is associated with at least one field of the one or more individually definable stimulation fields. Each field of the one or more individually definable stimulation fields is defined by a set of electrodes through a neurostimulation pulse is delivered. In various embodiments, each field of the one or more individually definable fields is defined by the set of electrodes through which the neurostimulation pulse is delivered and a current distribution of the neurostimulation pulse over the set of electrodes. In one embodiment, the current distribution is defined by assigning a fraction of an overall pulse amplitude to each electrode of the set of electrodes. In another embodiment, the current distribution is defined by assigning an amplitude value to each electrode of the set of electrodes. For example, the set of electrodes may include 2 electrodes used as the anode and an electrode as the cathode for delivering a neurostimulation pulse having a pulse amplitude of 4 mA. The current distribution over the 2 electrodes used as the anode needs to be defined. In one embodiment, a percentage of the pulse amplitude is assigned to each of the 2 electrodes, such as 75% assigned to electrode 1 and 25% to electrode 2. In another embodiment, an amplitude value is assigned to each of the 2 electrodes, such as 3 mA assigned to electrode 1 and 1 mA to electrode 2. Control of the current in terms of percentages allows precise and consistent distribution of the current between electrodes even as the pulse amplitude is adjusted. It is suited for thinking about the problem as steering a stimulation locus, and stimulation changes on multiple contacts simultaneously to move the locus while holding the stimulation amount constant. Control and displaying the total current through each electrode in terms of absolute values (e.g. mA) allows precise dosing of current through each specific electrode. It is suited for changing the current one contact at a time (and allows the user to do so) to shape the stimulation like a piece of clay (pushing/pulling one spot at a time).

Programming control circuit 816 represents an embodiment of programming control circuit 316 and generates the plurality of stimulation parameters, which is to be transmitted to implantable stimulator 704, based on the pattern of neurostimulation pulses as represented by one or more stimulation waveforms. The pattern may be created and/or adjusted by the user using user interface 810 and stored in external storage device 818. In various embodiments, programming control circuit 816 can check values of the plurality of stimulation parameters against safety rules to limit these values within constraints of the safety rules. In one embodiment, the safety rules are heuristic rules.

User interface 810 represents an embodiment of user interface 310 and allows the user to define the pattern of neurostimulation pulses and perform various other monitoring and programming tasks. User interface 810 includes a display screen 856, a user input device 858, and an interface control circuit 854. Display screen 856 may include any type of interactive or non-interactive screens, and user input device 858 may include any type of user input devices that supports the various functions discussed in this document, such as touchscreen, keyboard, keypad, touchpad, trackball, joystick, and mouse. In one embodiment, user interface 810 includes a GUI with an interactive screen that displays a graphical representation of a stimulation waveform and allows the user to adjust the waveform by graphically editing the waveform and/or various building blocks of the waveform. The GUI may also allow the user to perform any other functions discussed in this document where graphical editing is suitable as may be appreciated by those skilled in the art.

Interface control circuit 854 controls the operation of user interface 810 including responding to various inputs received by user input device 858 and defining the one or more stimulation waveforms. Interface control circuit 854 includes neurostimulation modules 320.

In various embodiments, external programming device 802 has operation modes including a composition mode and a real-time programming mode. Under the composition mode (also known as the pulse pattern composition mode), user interface 810 is activated, while programming control circuit 816 is inactivated. Programming control circuit 816 does not dynamically updates values of the plurality of stimulation parameters in response to any change in the one or more stimulation waveforms. Under the real-time programming mode, both user interface 810 and programming control circuit 816 are activated. Programming control circuit 816 dynamically updates values of the plurality of stimulation parameters in response to changes in the set of one or more stimulation waveforms, and transmits the plurality of stimulation parameters with the updated values to implantable stimulator 704.

Figures 9, 10:
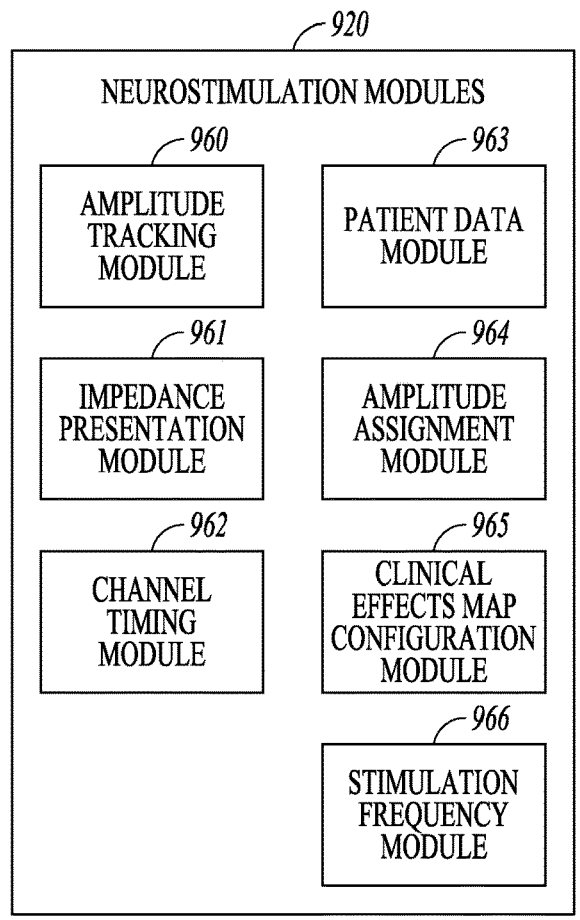
FIG. 9 illustrates an embodiment of portions of a circuit of a user interface of a programming device, such as the external programming device of FIG. 8.
FIG. 10 illustrates an embodiment of portions of a screen displaying electrode impedances.

FIG. 9 illustrates an embodiment of neurostimulation modules 920, which represent an embodiment of neurostimulation modules 320. In the illustrated embodiment, neurostimulation modules 920 includes an amplitude tracking module 960, an impedance presentation module 961, a channel timing module 962, a patent data module 963, an amplitude assignment module 964, and a clinical effects map configuration module 965. In various embodiments, neurostimulation modules 920 may include any one or any combination of amplitude tracking module 960, impedance presentation module 961, channel timing module 962, patent data module 963, amplitude assignment module 964, clinical effects map configuration module 965, a stimulation frequency module 966, and one or more other functional modules configured to be used in programming a stimulation device for neurostimulation. In various embodiments, such modules may be used individually or in any combination to facilitate the process of defining the one or more stimulation waveforms, and hence the plurality of stimulation parameters, that represent the pattern of neurostimulation pulses to be delivered to the patient during a neurostimulation therapy session.

It is to be understood that while neurostimulation modules 920, including amplitude tracking module 960, impedance presentation module 961, channel timing module 962, patient data module 963, amplitude assignment module 964, and clinical effects map configuration module 965, are discussed as part of user interface 810, other portions of external programming device 802 may be configured to perform at least some of the functions discussed under neurostimulation modules 920 without departing from the scope of the present subject matter. In other words, the arrangement of amplitude tracking module 960, impedance presentation module 961, channel timing module 962, patent data module 963, amplitude assignment module 964, and clinical effects map configuration module 965 are illustrated in FIG. 9 by way of example, but not by way of limitation, as in various embodiments, the various functions of these modules may each be partially or wholly performed by a circuit that is not necessarily considered to be part of user interface 810.

Amplitude tracking module 960 allows the user to set patient-specific minimum and maximum pulse amplitudes for the neurostimulation pulses using user interface 810. In one embodiment, a CP, such as CP 630, is configured to allow the user to limit the pulse amplitudes each in terms of a percentage increase or decrease from an initial programmed amplitude or in terms of an absolute maximum or minimum value. An RC, such as RC 632, is configured to record the maximum and minimum pulse amplitudes set by the user each as an absolute value (rather than a percentage or other relative value), so that the amplitude limits may be preserved when the patient adjusts the pulse amplitude using the RC. This is because the pulse amplitude set in the RC may change as the patient adjusts stimulation within the limits set by the user.

In various embodiments, amplitude tracking module 960 also controls display of the minimum and maximum pulse amplitudes on display screen 856. In various embodiments, the minimum and maximum pulse amplitudes may be displayed on display screen 856 as markers on a button or controller for the pulse amplitude, markers on a clinical effects map, or boundaries on a 3-dimensional representation of the stimulation field. An example of setting and displaying the minimum and maximum pulse amplitudes is discussed in U.S. Provisional Patent Application Ser. No. 62/130,037, entitled "DEEP BRAIN STIMULATION CLINICAL EFFECTS MAP WITH VISUAL INDICATORS FOR PATIENT AMPLITUDE LIMITS", filed on Mar. 9, 2015, assigned to Boston Scientific Neuromodulation Corporation, which is incorporated by reference in its entirety.

Impedance presentation module 961 controls display of various lead/electrode impedance values on display screen 856. The impedance on an electrode can be measured in operating a neurostimulation system to confirm device functionality such as proper delivery of neurostimulation. For example, open-circuit and short-circuit are two device failures that can be detected by checking electrode impedance. These two types of failures are best detected using two different kinds of impedance measurement. Open circuits may be more easily detected by measuring monopolar impedance (e.g., the impedance between one of electrodes 406 and one of electrodes 426 and 428 as illustrated in FIG. 4). Short circuits may require measurement of bipolar impedances (e.g., the impedance between two electrodes of electrodes 406 as illustrated in FIG. 4). Such impedance measurements may be performed, for example, by implantable stimulator 704 alone or by implantable stimulator 704 and external programming device 802. Impedance presentation module 961 can receive the measured impedance values and arrange these impedance values for display on display screen 856. In various embodiments, impedance presentation module 961 arranges these impedance values to be displayed in an intuitive and user-friendly way to facilitate the use of such impedance values as part of the basis for neurostimulation programming, such as by allowing the user to identify potentially problematic electrodes and determine a need to replace the problematic lead or defining the one or more stimulation fields in a way obviating the potential problem.

FIG. 10 illustrates an embodiment of a portion of display screen 856 displaying "N-Polar Impedance". For the purpose of illustration, impedance measurements for 8 lead electrodes E1-E8 (such as electrodes 406 as illustrated in FIG. 4) and an additional electrode (such as one of electrodes 426 and 428 as illustrated in FIG. 4) are shown. It is noted that the values as shown in FIG. 10 are arbitrary numbers for illustration purposes only. In the illustrated embodiment, impedances on every combination of electrodes are measured and displayed in a matrix, with the diagonal of the matrix representing monopolar impedances and the rest of the matrix representing bipolar impedances on for the electrodes in that row and column. For example, the monopolar impedance for electrode E2 is 524Ω, and the bipolar impedance between electrodes E2 and E7 is 702Ω. For the bipolar impedances, only the values above the diagonal is shown as the values below the diagonal are identical (e.g., bipolar impedance between electrodes E2 and E7 and the bipolar impedance between electrodes E7 and E2 are the same impedance). In various embodiments, the bipolar impedances may be displayed only above the diagonal, only below the diagonal, or for the entire matric (with redundancy). In various other embodiments, the matrix can also display the additional electrode (such as one of electrodes 426 and 428 as illustrated in FIG. 4), and the monopolar impedances can be displayed as impedances each between one of the lead electrodes and the additional electrode.

The format of the "N-Polar Impedance" display as shown in FIG. 10 is illustrated by way of example, but not way of limitation. In various embodiments, impedance presentation module 961 can arrange for display of impedances for all the combinations of electrodes or selected combinations of electrodes. In various embodiments, impedance presentation module 961 can arrange the impedance values to be displayed in any format that allows visual inspection by the user.

Channel timing module 962 controls area relative timing. Implantable stimulator 704 can deliver the neurostimulation pulses through multiple timing channels. For example, stimulation output circuit 212 can include the multiple timing channels each to be electrically coupled to one or more electrodes of electrodes 706. The plurality of stimulation parameters may be set, as desirable, for each timing channel to deliver pulses at a pre-defined rate, such that pulses from different channels arrive at certain intervals relative to each other. To ensure that these relative intervals remain constant, channel timing module 962 starts a "turn-off" period for all the active timing channels in response to a timing channel being activated or inactivated, followed by an ordered activation of each channel. In other words, when delivery of pulses from one of the timing channels of stimulation output circuit 212 starts or ends, the delivery of pulses from all the timing channels of stimulation output circuit 212 is to be suspended, for example for the current cycle (with the "cycle" being pre-defined such as by a sequence of pulses from different timing channels that is to be repeated), and restarts from the next cycle. This ensures that the relative intervals between the timing channels do not vary depending on the sequence of activation.

Figure 11:
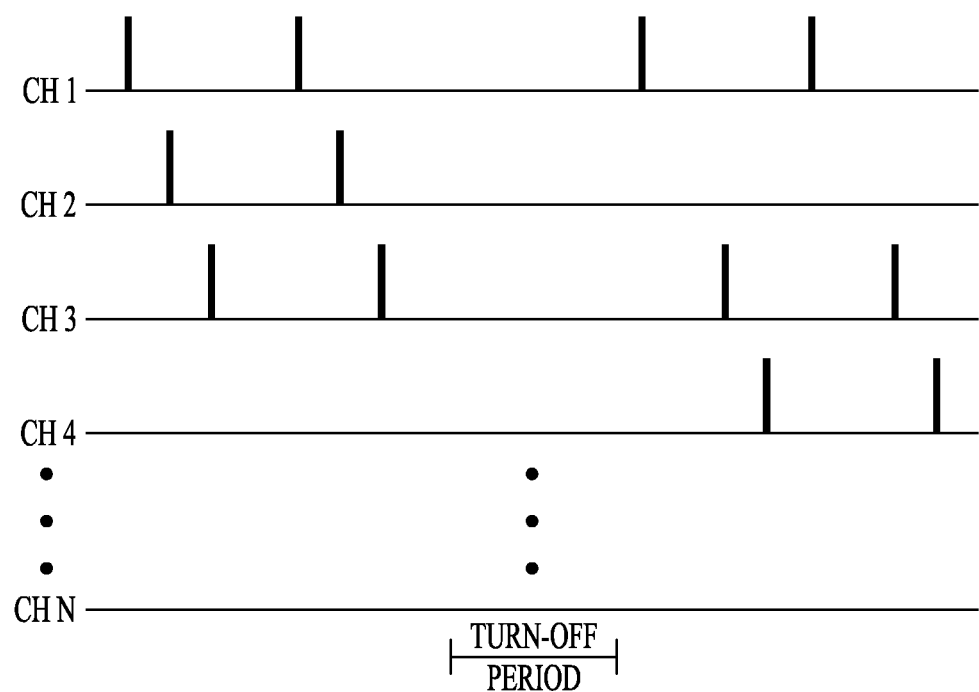
FIG. 11 illustrates an embodiment of area relative timing in delivering neurostimulation pulses.

FIG. 11 illustrates an embodiment of area relative timing in delivering neurostimulation pulses. Illustrated by way of example, but not by way of limitation, a timing diagram in FIG. 11 shows a segment of a pattern of neurostimulation pulses where pulses are first delivered from timing channels 1-3 (CH1-CH3). Then, timing channel 2 (CH 2) is to be inactivated, and timing channel 4 (CH4) is to be activated. This change of channel activation triggers the turn-off period as shown in FIG. 11, during which the delivery of pulses are suspended for all the timing channels. Upon the end of the turn-off channel, the delivery of pulses is resumed according to the new sequence of activation with timing channel 2 being inactive and timing channel 4 being active.

In various embodiments, channel timing module 962 can incorporate the area relative timing, such as discussed above, into the one or more stimulation waveforms that may be defined using user interface 810. In one embodiment, channel timing module 962 asks the user for whether to apply the area relative timing to one or more stimulation waveforms being defined using user interface 810, such as by presenting a message with an answering field on display screen 856. When the area relative timing is to be applied, channel timing module 962 identifies one or more transition points that meet specified criteria for applying the area relative timing (e.g., points of channel activation or inactivation) in the one or more stimulation waveforms and introduces the turn-off period to each point of the identified transition points. In another embodiment, channel timing module 962 automatically applies the area relative timing to all the stimulation waveforms for neurostimulation without necessarily checking with the user.

Patient data module 963 allows the user to access the patient information stored in implantable stimulator 704 using user interface 810. In various embodiments, patient data module 963 can allow the user to view the patient information stored in implant storage device 746. In various embodiments, patient data module 963 can also allow the user to make addition to, deletion from, and/or modification of the patient information stored in implant storage device 746 upon authorization (for example as obtained using a pre-authorized username and password). In various embodiments, this allows external programming device (such as may be implemented as CP 630) to be used in a way similar to a computer configured as a terminal for an electronic medical record system such as used in a hospital of clinic. In various embodiments, patient data module 963 allows the user to obtain information necessary or desirable for neurostimulation programming.

In one embodiment, patient data module 963 can present a menu listing categories and/or titles of contents of the patient information stored in implantable stimulator 704. Examples of categories include general information such as patient demographics and general medical history as well as information specific to the indications for DBS such as brain images, clinical effect maps, and data of quantitative measurements specific to the indications for neurostimulation.

Amplitude assignment module 964 allows the user to assign, using user interface 810, an amplitude value to each electrode used for delivering a neurostimulation pulse in the process of defining the one or more stimulation fields, thereby controlling current steering. When a neurostimulation pulse is delivered through multiple electrodes functioning as an anode or cathode for that pulse, the current distribution needs to be specified for each of the multiple electrodes as part of the definition of the stimulation field. In one embodiment, a single pulse amplitude is specified for the neurostimulation pulse, and amplitude assignment module 964 allows that pulse amplitude to be fractionally assigned to the multiple electrodes, such as a percentage for each electrode of the multiple electrodes. In another embodiment, which may be referred to as a "milliamp mode", amplitude assignment module 964 allows an absolute amplitude value to be independently assigned to each electrode of the multiple electrodes.

Clinical effects map configuration module 965 receives a selection of a target for the neurostimulation (such as DBS) and/or an indication for the neurostimulation (such as a disease known as being treatable by DBS), and automatically configures a clinical effects map based on the selection. The clinical effects map indicates efficacy and side effects of DBS. In various embodiments, because different indications (e.g., neuropsychiatric indications) may be associated with symptoms different than movement disorders, clinical effects map configuration module 965 automatically configures the list of therapeutic effects based on the selected indication. Because side effects are a function of unwanted stimulation of nearby structures, which will vary depending on the anatomical location of the target for DBS, clinical effects map configuration module 965 automatically configures the side effect list based on the selected indication or target.

Figure 12:
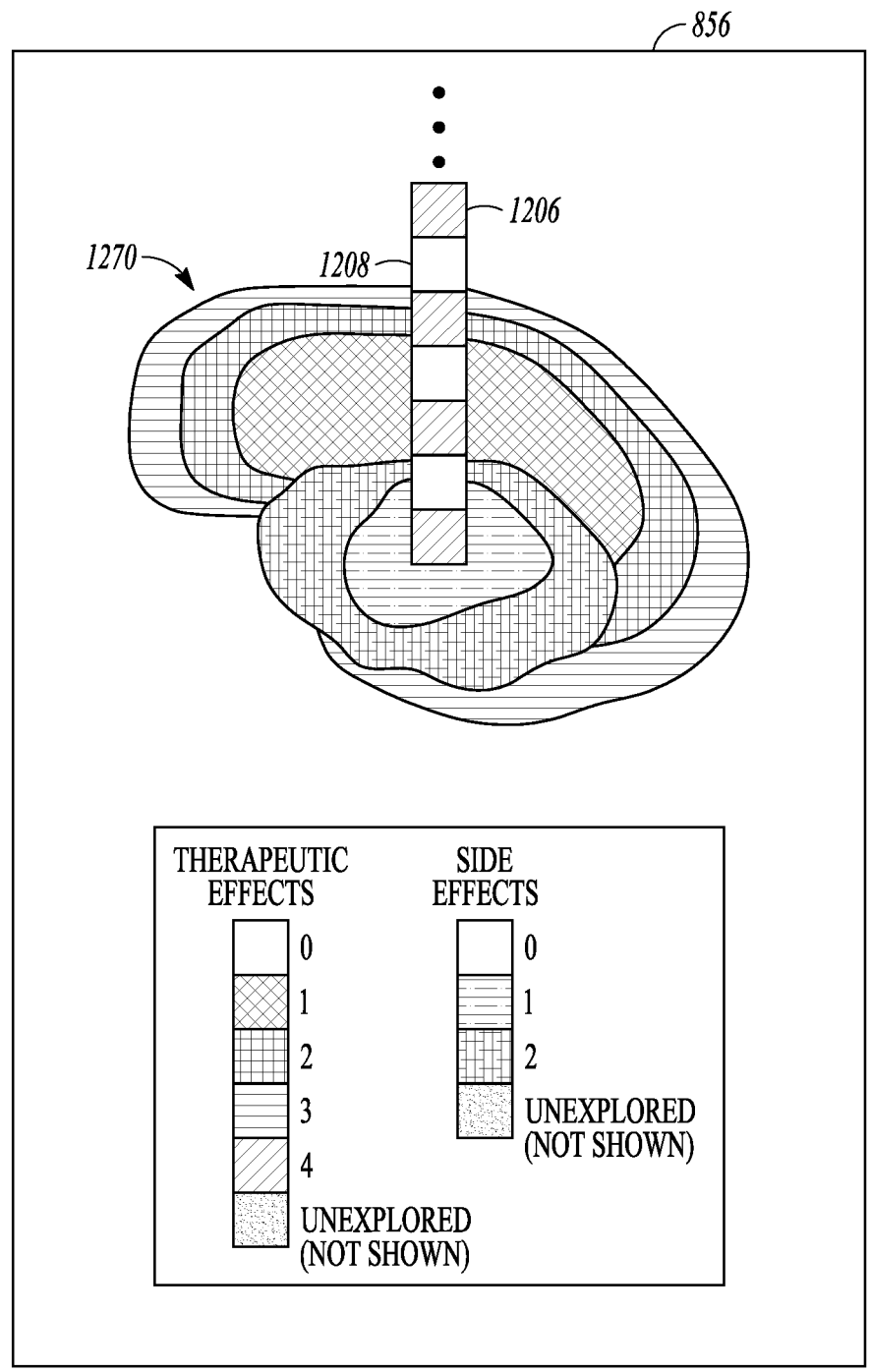
FIG. 12 illustrates an embodiment of portions of a screen displaying a clinical effects map.

FIG. 12 illustrates an embodiment of portions of display screen 856 displaying an example of such a clinical effects map 1270. An example of producing and visually presenting a clinical effects map such as map 1270 is discussed in U.S. Patent Application Publication No. US 2014/0066999 A1, entitled "CAPTURE AND VISUALIZATION OF CLINICAL EFFECTS DATA IN RELATION TO A LEAD AND/OR LOCUS OF STIMULATION", filed on Aug. 28, 2013, assigned to Boston Scientific Neuromodulation Corporation, which is incorporated by reference in its entirety. In FIG. 12, a model of a lead 1208 with electrodes 1206 is displayed, and maps showing volume of activations are displayed overlaid on the model of the lead. Therapeutic efficacy and adverse side-effects of stimulations are evaluated for a plurality of points about lead 1208 based on clinical data resulting from the stimulations to estimate the volume of activation for the stimulations. Clinical effects map as shown in FIG. 12 is a combination of maps each associated with one of the therapeutic effects or side effects. In various embodiments, the map for each therapeutic or side effect may also be individually displayed.

In various embodiments, clinical effects map configuration module 965 may be configured to display one or more clinical effects maps in any format that is suitable for indicating efficacy and side effects of DBS to the user for DBS programming, with clinical effects map 1270 illustrated in FIG. 12 as one example. In some embodiments, clinical effects map configuration module 965 allows the user to select a format of clinical effects map for display on display screen 856 from a plurality of formats. In various embodiments, the clinical effects map is indicative of therapeutic and side effects of DBS with respect to each of various stimulation parameters and stimulation fields based on which the user can determine values for the stimulation parameters and selections of electrodes for maximizing therapeutic effects while minimizing side effects.

Stimulation frequency module 966 allows the user to control stimulation frequency (also referred to as rate) at which the neurostimulation pulses are delivered. In various embodiments, stimulation frequency module 966 allows the user to select between a single frequency mode and a multiple frequency mode. Under the single frequency mode, an adjustment of stimulation frequency in one area of stimulation (e.g., one stimulation field) causes an equivalent change in the stimulation frequency in all the areas of stimulation (e.g., all the stimulation fields) in a neurostimulation session, such that only one stimulation frequency is used at a time. Under the multiple frequency mode, an adjustment of stimulation frequency in one area of stimulation (e.g., one stimulation field) affects the stimulation frequency associated with that area only and does not cause change in the stimulation frequency for another area (e.g., another stimulation field) in a neurostimulation therapy session. In various embodiments that use multiple areas of stimulations in a neurostimulation therapy session, stimulation frequency module 966 computes compatible rates for each area of stimulation and displays them in one or more stimulation rate tables on display screen 856. The compatible (or available) rates for an area of stimulation are stimulation frequencies available for use based on the neurostimulation pulses delivered to all the areas of stimulation. The incompatible (or unavailable) rates may also be displayed, but are not selectable for use. An example of the incompatible rates includes stimulation frequencies at which two or more pulses of the neurostimulation pulses will be delivered to different areas of stimulation simultaneously (i.e., at least partially overlapping in time). Simultaneous delivery of stimulation pulses may decrease therapeutic effectiveness of the neurostimulation.

FIG. 13 illustrates an embodiment of portions of display screen 856 displaying an example of such a stimulation rate table (also referred to as stimulation frequency table) 1372. Stimulation rate table 1372 presents stimulation frequencies (i.e., rates) for an area of stimulation. In various embodiments, stimulation frequency module 966 limits the stimulation frequencies according to a cumulative rate per lead rule. Under the cumulative rate per lead rule, the user can select any stimulation frequency (i.e., rate) for the areas of stimulation (field) corresponding to a given lead such that the sum of the stimulation frequencies associated with that lead is below a threshold, which may be specified based on safety considerations. An example of the threshold is about 255 Hz. In various embodiments, the threshold may be determined based on data from safety studies. In various other embodiments, the cumulative rate (sum of the stimulation frequencies) may be limited for each electrode or a set of electrodes.

When operating in the multiple frequency mode, it is desirable to prevent pulses from different timing channels from being delivered simultaneously (such that two or more pulses overlap in time). In one embodiment, stimulation frequency module 966 provides for (1) a limitation option, in which the available combinations of stimulation frequencies are limited, or (2) an arbitration option, in which timing of delivery of neurostimulation pulses from a timing channel can be slightly modified (e.g., delayed) when needed, introducing some variability in the inter-pulse interval (IPI) for that timing channel. In one embodiment, stimulation frequency module 966 allows the user to select between the limiting and arbitration options, i.e., (1) and (2). When the arbitration option is selected, stimulation frequency module 966 causes the degree of the variability in IPI for any combination of stimulation frequencies on display screen 856 as a percentage of the stimulation pulses that are delayed, as a standard deviation in the IPI, and/or through other descriptive statistics.

In the illustrated embodiment, stimulation rate table 1372 includes all the stimulation frequencies, with each of the stimulation frequencies indicated to be (a) selected, (b) available for selection (compatible), or (c) unavailable for selection (incompatible) or available for selection after arbitration. Examples for (a), (b), and (c) are illustrated in FIG. 13 as displaying areas 1374, 1376, and 1378, respectively, in which each stimulation frequency is indicated to be one of (a), (b), or (c) using gray scale. In other embodiments, each stimulation frequency may be indicated to be one of (a), (b), or (c) using color, pattern, or any other visually distinguishable features. If the user selects the limitation option, the stimulation frequencies indicated to be (c), e.g., 1378, are displayed but not selectable by the user. If the user selects the arbitration option, the stimulation frequencies indicated to be (c), e.g., 1378, as displayed are each selectable by the user but associated with a modification of timing (e.g., introduction of delays) in delivering the neurostimulation pulses resulting from the arbitration. In various embodiments, stimulation frequency module 966 causes the plurality of stimulation frequencies to be displayed on screen 856 with each stimulation frequency visually indicated to be (a), (b), or (c). When the arbitration option is selected, stimulation frequency module 966 causes the plurality of stimulation frequencies to be displayed on screen 856 with visual indications for the stimulation frequencies to which the arbitration is performed and/or the degree to which arbitration is performed for that combination of stimulation frequencies.

In one embodiment, stimulation rate table 1372 allows for selection of all stimulation frequencies, including stimulation frequencies for which the arbitration is performed. No stimulation frequency is unavailable in stimulation rate table 1372 (i.e., all the stimulation frequencies are selectable), but the stimulation frequencies for which the arbitration is performed are indicated in stimulation rate table 1372. In one embodiment, the stimulation frequencies for which the arbitration is performed are indicated with showing of the degree of resulting variability in the IPI in stimulation rate table 1372.

In various embodiments, using stimulation rate table 1372 allows the user to skip directly to desired stimulation frequencies without having to pass through unwanted combinations of frequencies. Stimulation rate table 1372 also allows the user to compare a complete list of available combinations of the stimulation frequencies before choosing the best combination.

In various embodiments, neurostimulation modules 920 may include any one or any combination of the functional modules discussed above and/or one or more other functional modules configured to be used in programming a stimulation device for neurostimulation. In addition to the Examples 1-25 discussed in the Summary Section above, some other non-limiting examples are provided as follows.

An example (e.g., "Example 21") of a system for delivering neurostimulation pulses to a patient using a plurality of electrodes and controlling the delivery of the neurostimulation pulses by a user may include a programming control circuit and a user interface. The programming control circuit may be configured to generate a plurality of stimulation parameters controlling delivery of neurostimulation pulses according to one or more stimulation waveforms. The interface may include a display screen and an interface control circuit. The interface control circuit may be configured to define the one or more stimulation waveforms, and may include an impedance presentation module. The impedance presentation module may be configured to receive values of impedances each between two electrodes of the plurality of electrodes for all of combinations of two electrodes available from the plurality of electrodes and display the received values of impedances on the display screen.

In Example 22, the subject matter of Example 21 may optionally be configured to further include an implantable stimulator and an implantable lead. The implantable stimulator may include a stimulation output circuit configured to deliver the neurostimulation pulses and a stimulation control circuit configured to control the delivery of the neurostimulation pulses using the plurality of stimulation parameters. The implantable lead may be configured to be connected to the implantable stimulator and include a plurality of lead electrodes of the plurality of electrodes.

In Example 23, the subject matter of Example 22 may optionally be configured such that the implantable stimulator further includes a reference electrode of the plurality of electrodes, and the impedance presentation module is configured to receive and display values of monopolar impedances each between an electrode of the plurality of lead electrodes and the reference electrode and values of bipolar impedances each between two electrodes of the plurality of lead electrodes.

In Example 24, the subject matter of Example 23 may optionally be configured such that the impedance presentation module is configured display the received values of impedances on the display screen in a matrix showing all the monopolar impedances and bipolar impedances with the monopolar impedances shown along the diagonal of the matrix.

In Example 25, the subject matter of any one or any combination of Examples 22-24 may optionally be configured such that the stimulation output circuit includes a plurality of timing channels each configured to deliver pulses of the neurostimulation pulses when being programmed to be active and not to deliver pulses of the neurostimulation pulses when being programmed to be inactive, and the interface control circuit includes a channel timing module configured to identify one or more transition points in the one or more stimulation waveforms at which a timing channel of the plurality of timing channels becomes active or becomes inactive and apply a turn-off period during which none of the neurostimulation pulse is delivered from any active channel of the plurality of timing channels to each point of the identified one or more transition points, so that relative timing between the pulses delivered from channels that remain active before and after a point of the identified one or more transition points remain unchanged.

In Example 26, the subject matter of any one or any combination of Examples 22-24 may optionally be configured to further include an external programming device configured to be communicatively coupled to the implantable stimulator via telemetry. The external programming device includes the programming control circuit and the user interface.

In Example 27, the subject matter of Example 26 may optionally be configured such that the external programming device is configured to be communicatively coupled to the implantable stimulator via a wireless communication link using far-field radio frequency telemetry.

In Example 28, the subject matter of any one or any combination of Examples 26 and 27 may optionally be configured such that the external programming device is configured to transmit patient information to the implantable stimulator via the wireless communication link, and the implantable stimulator further includes an implant storage device configured to store the received patient information, the patient information including portions of the patient's electronic medical records.

In Example 29, the subject matter of Example 28 may optionally be configured such that the implantable stimulator is configured to produce data to add to the patient information stored in the implant storage device.

In Example 30, the subject matter of Example 28 may optionally be configured such that the interface control circuit includes a patient data module configured to allow the user to retrieve the patient information from the implantable stimulator using the user interface. The patient data module may be configured to allow the user to select portions of the patient information for presentation using the display screen.

In Example 31, the subject matter of any one or any combination of Examples 21-30 may optionally be configured such that the interface control circuit includes an amplitude assignment module configured to assign pulse amplitudes each to an electrode of a set of electrodes selected from the plurality of electrodes for delivering a pulse of the neurostimulation pulses in terms of absolute values.

In Example 32, the subject matter of any one or any combination of Examples 21-31 may optionally be configured such that the interface control circuit includes a clinical effects map configuration module configured to configure a clinic effects map indicative of therapeutic effects and side effects estimated for the one or more stimulation waveforms.

In Example 33, the subject matter of Example 32 may optionally be configured such that the clinical effects map configuration module is configured to receive a selection of an indication for neurostimulation and automatically update the therapeutic effects based on the selected indication.

In Example 34, the subject matter of Example 32 may optionally be configured such that the clinical effects map configuration module is configured to receive a selection of a target for neurostimulation or a selection of an indication for the neurostimulation and automatically update the side effects based on the selected target or the selected indication.

In Example 35, the subject matter of any one or any combination of Examples 21-34 may optionally be configured such that the interface control circuit includes an amplitude tracking module configured to allow the user to set minimum and maximum pulse amplitudes for the neurostimulation pulses using the user interface.

An example (e.g., Example 36") of a method for programming an implantable stimulator to deliver neurostimulation pulses to a patient using a plurality of electrodes is also provided. The method includes programming an implantable stimulator for delivering electrical pulses through a plurality of electrodes using an external programming device, and presenting information for the programming using the user interface of the external programming device. The presentation of the information includes displaying values of impedances each between two electrodes of the plurality of electrodes for all of combinations of two electrodes available from the plurality of electrodes and displaying the received values of impedances on the display screen.

In Example 37, the subject matter of Example 36 may optionally include delivering the electrical pulses using a plurality of timing channels of the implantable stimulator, the plurality of timing channels each configured to deliver one or more of the electrical pulses when being programmed to be active and none of the electrical pulses when being programmed to be inactive, identifying one or more transition points in the one or more stimulation waveforms at which a timing channel of the plurality of timing channels becomes active or becomes inactive, and applying a turn-off period during which none of the electrical pulse is delivered from any active channel of the plurality of timing channels to each point of the identified one or more transition points, so that relative timing between the pulses delivered from channels that remain active before and after a point of the identified one or more transition points remain unchanged.

In Example 38, the subject matter of any one or any combination of Examples 36 and 37 may optionally include providing for wireless communication between the implantable stimulation and the external programming device using far-field radio frequency telemetry.

In Example 39, the subject matter of any one or any combination of Examples 36-38 may optionally include transmitting patient information to the implantable stimulator via the wireless communication link and storing the received patient information in a storage device in the implantable stimulator. The patient information includes portions of the patient's electronic medical records including information specific to indications for neurostimulation.

In Example 40, the subject matter of any one or any combination of Examples 36-39 may optionally include assigning pulse amplitudes each to an electrode of a set of electrodes selected from the plurality of electrodes for delivering a pulse of the electrical pulses in terms of absolute values.

In Example 41, the subject matter of any one or any combination of Examples 36-39 may optionally include automatically configuring a clinic effects map indicative of therapeutic effects and side effects estimated for the one or more stimulation waveforms based on a selection of a target for neurostimulation or a selection of an indication for the neurostimulation.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for delivering neurostimulation pulses to a patient using a plurality of electrodes and controlling the delivery of the neurostimulation pulses by a user, the system comprising:
   a programming control circuit configured to generate a plurality of stimulation parameters controlling delivery of neurostimulation pulses according to one or more stimulation waveforms;
   a user interface including:
      a display screen; and
      an interface control circuit configured to define the one or more stimulation waveforms, the interface control circuit including an impedance presentation module configured to determine values of impedances each between two electrodes of the plurality of electrodes for all combinations of two electrodes available from the plurality of electrodes and to display all the determined values of impedances on the display screen;
   an implantable stimulator including:
      a stimulation output circuit configured to deliver the neurostimulation pulses; and
      a stimulation control circuit configured to control the delivery of the neurostimulation pulses using the plurality of stimulation parameters; and
   an implantable lead configured to be connected to the implantable stimulator and including a plurality of lead electrodes of the plurality of electrodes,
   wherein the stimulation output circuit includes a plurality of timing channels each configured to deliver pulses of the neurostimulation pulses when being programmed to be active and not to deliver pulses of the neurostimulation pulses when being programmed to be inactive, and the interface control circuit includes a channel timing module configured to identify one or more transition points in the one or more stimulation waveforms at which a timing channel of the plurality of timing channels becomes active or becomes inactive and apply a turn-off period during which none of the neurostimulation pulse is delivered from any active channel of the plurality of timing channels to each point of the identified one or more transition points, so that relative timing between the pulses delivered from channels that remain active before and after a point of the identified one or more transition points remain unchanged.

2. The system of claim 1, wherein the implantable stimulator further comprises a reference electrode of the plurality of electrodes, and the impedance presentation module is configured to determine and display values of monopolar impedances each between an electrode of the plurality of lead electrodes and the reference electrode and values of bipolar impedances each between two electrodes of the plurality of lead electrodes.

3. The system of claim 2, wherein the impedance presentation module is configured display the determined values of impedances on the display screen in a matrix showing all the monopolar impedances and bipolar impedances with the monopolar impedances shown along a diagonal of the matrix.

4. The system of claim 1, further comprising an external programming device configured to be communicatively coupled to the implantable stimulator via telemetry, the external programming device including the programming control circuit and the user interface.

5. The system of claim 4, wherein the external programming device is configured to be communicatively coupled to the implantable stimulator via a wireless communication link using far-field radio frequency telemetry.

6. The system of claim 4, wherein the external programming device is configured to transmit patient information to the implantable stimulator via the wireless communication link, and the implantable stimulator further comprises an implant storage device configured to receive and store the transmitted patient information, the patient information including portions of the patient's electronic medical records.

7. The system of claim 6, wherein the interface control circuit comprises a patient data module configured to allow the user to retrieve the patient information from the implantable stimulator using the user interface, the patient data module configured to allow the user to select portions of the patient information for presentation using the display screen.

8. The system of claim 1, wherein the interface control circuit comprises an amplitude assignment module configured to assign pulse amplitudes each to an electrode of a set of electrodes selected from the plurality of electrodes for delivering a pulse of the neurostimulation pulses in terms of absolute values.

9. The system of claim 1, wherein the interface control circuit comprises a clinical effects map configuration module configured to configure a clinic effects map indicative of therapeutic effects and side effects estimated for the one or more stimulation waveforms.

10. The system of claim 9, wherein the clinical effects map configuration module is configured to receive a selection of an indication for neurostimulation and automatically update the therapeutic effects based on the selected indication.

11. The system of claim 9, wherein the clinical effects map configuration module is configured to receive a selection of a target for neurostimulation or a selection of an indication for the neurostimulation and automatically update the side effects based on the selected target or the selected indication.

12. A method for programming an implantable stimulator to deliver neurostimulation pulses to a patient using a plurality of electrodes, the method comprising:
   programming the implantable stimulator for delivering electrical pulses through a plurality of electrodes using an external programming device;
   presenting information for the programming using a user interface of the external programming device, including displaying values of impedances each between two electrodes of the plurality of electrodes for all combinations of two electrodes available from the plurality of electrodes and displaying all the determined values of impedances, on a display screen of the user interface;
   delivering the electrical pulses using a plurality of timing channels of the implantable stimulator, the plurality of timing channels each configured to deliver one or more of the electrical pulses when being programmed to be active and none of the electrical pulses when being programmed to be inactive;
   identifying one or more transition points in the one or more stimulation waveforms at which a timing channel of the plurality of timing channels becomes active or becomes inactive; and
   applying a turn-off period during which none of the electrical pulse is delivered from any active channel of the plurality of timing channels to each point of the identified one or more transition points, so that relative timing between the pulses delivered from channels that remain active before and after a point of the identified one or more transition points remain unchanged.

13. The method of claim 12, comprising providing for wireless communication between the implantable stimulation and the external programming device using far-field radio frequency telemetry.

14. The method of claim 12, comprising:
   transmitting patient information to the implantable stimulator via the wireless communication link; and
   storing the patient information in a storage device in the implantable stimulator,
   wherein the patient information includes portions of the patient's electronic medical records including information specific to indications for neurostimulation.

15. The method of claim 12, comprising assigning pulse amplitudes each to an electrode of a set of electrodes selected from the plurality of electrodes for delivering a pulse of the electrical pulses in terms of absolute values.

16. The system of claim 12, comprising automatically configuring a clinic effects map indicative of therapeutic effects and side effects estimated for the one or more stimulation waveforms based on a selection of a target for neurostimulation or a selection of an indication for the neurostimulation.

17. A non-transitory computer-readable storage medium including instructions, which when executed by a system, cause the system to perform a method for programming an implantable stimulator to deliver neurostimulation pulse using a plurality of electrodes, the method comprising:
   programming the implantable stimulator for delivering electrical pulses through a plurality of electrodes using an external programming device; and
   presenting information for the programming using a user interface of the external programming device, including displaying values of impedances each between two electrodes of the plurality of electrodes for all combinations of two electrodes available from the plurality of electrodes and displaying all the determined values of impedances, on a display screen of the user interface;
   delivering the electrical pulses using a plurality of timing channels of the implantable stimulator, the plurality of timing channels each configured to deliver one or more of the electrical pulses when being programmed to be active and none of the electrical pulses when being programmed to be inactive;
   identifying one or more transition points in the one or more stimulation waveforms at which a timing channel of the plurality of timing channels becomes active or becomes inactive; and
   applying a turn-off period during which none of the electrical pulse is delivered from any active channel of the plurality of timing channels to each point of the identified one or more transition points, so that relative timing between the pulses delivered from channels that remain active before and after a point of the identified one or more transition points remain unchanged.

18. The non-transitory computer-readable storage medium of claim 17, wherein the method further comprises:
   transmitting patient information to the implantable stimulator via the wireless communication link; and
   storing the patient information in a storage device in the implantable stimulator,
   wherein the patient information includes portions of the patient's electronic medical records including information specific to indications for neurostimulation.

19. The non-transitory computer-readable storage medium of claim 17, wherein the method further comprises assigning pulse amplitudes each to an electrode of a set of electrodes selected from the plurality of electrodes for delivering a pulse of the electrical pulses in terms of absolute values.

20. The non-transitory computer-readable storage medium of claim 17, wherein the method further comprises automatically configuring a clinic effects map indicative of therapeutic effects and side effects estimated for the one or more stimulation waveforms based on a selection of a target for neurostimulation or a selection of an indication for the neurostimulation.

* * * * *